United States Patent [19]

Miller et al.

[11] Patent Number: 4,496,785
[45] Date of Patent: Jan. 29, 1985

[54] PROCESS FOR REACTING ALCOHOLS AND OLEFINS

[75] Inventors: Jeffrey T. Miller; Thomas D. Nevitt, both of Naperville, Ill.

[73] Assignee: Standard Oil Company (Indiana), Chicago, Ill.

[21] Appl. No.: 536,671

[22] Filed: Sep. 28, 1983

[51] Int. Cl.$^3$ ................................................ C07C 1/22
[52] U.S. Cl. ................................... 585/640; 585/408; 585/415; 585/418; 585/469; 585/275; 585/671; 585/733; 585/739; 502/340
[58] Field of Search ............... 585/415, 408, 417, 418, 585/469, 275, 262, 671, 670, 640, 733, 739; 502/340

[56] References Cited

U.S. PATENT DOCUMENTS 3,444,257  5/1969  Engelhard ........................ 585/262
3,871,993  3/1975  Morrison .......................... 585/415
3,894,104  7/1975  Chang et al. ..................... 585/408
4,292,458  9/1981  Klotz ................................ 585/469

FOREIGN PATENT DOCUMENTS 1894979  5/1975  United Kingdom ............... 585/415

Primary Examiner—Delbert E. Gantz
Assistant Examiner—Asokkumar Pal
Attorney, Agent, or Firm—James R. Henes; William H. Magidson; William T. McClain

[57] ABSTRACT

A method for producing branched aliphatic hydrocarbons by reacting $H_2$ with a $C_1$–$C_6$ alcohol and/or a $C_2$–$C_6$ olefin in the presence of a cadmium component and a support which comprises an amorphous refractory inorganic oxide, a pillared smectite or vermiculite clay, a molecular sieve consisting essentially of unexchanged or cation-exchanged chabazite, clinoptilite, zeolite A, zeolite L, zeolite X, zeolite Y, ultrastable zeolite Y, or crystalline borosilicate molecular sieve, or a combination thereof.

19 Claims, No Drawings

PROCESS FOR REACTING ALCOHOLS AND OLEFINS

BACKGROUND OF THE INVENTION

1. Field of the Invention

This invention relates generally to the reaction between hydrogen and at least one of an alcohol containing from 1 to 6 carbon atoms and an olefin containing from 2 to 6 carbon atoms, and more particularly concerns such reaction in the presence of a cadmium-containing catalyst.

2. Description of the Prior Art

The production from less valuable materials of aliphatic compounds boiling in the gasoline range, of aromatic compounds, and of intermediates useful for the production of such aliphatic and aromatic compounds, is highly desirable and has been the object of several prior art methods involving the use of cadmium-containing catalysts. For example, Woodruff et al., U.S. Pat. Nos. 1,625,924 and 1,625,928, disclose a method for producing methanol by reacting oxides of carbon with hydrogen at high pressures and in the presence of a catalyst comprising one or more non-reducible metal oxides, such as zinc, magnesium, cadmium, chromium, vanadium, or tungsten, and one or more easily reducible metal oxides, such as copper, silver, iron, nickel, or cobalt, and a metallic halide. Melaven et al., U.S. Pat. No. 2,301,735, disclose a process for converting heavy hydrocarbon oils into gasoline by contacting the heavy oils with a catalyst comprising silica impregnated with a cadmium compound.

Klotz, U.S. Pat. No. 4,269,813, discloses a crystalline borosilicate catalyst comprising a molecular sieve material having the following composition in terms of mole ratios of oxides:

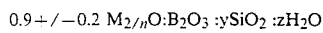

wherein M is at least one cation, n is the valence of the cation, y is a value within the range of 4 to about 600, and z is a value within the range of 0 to about 160, and providing a specific X-ray defraction pattern. M represents an alkali metal cation, an alkaline earth metal cation, an ammonium cation, an alkylammonium cation, a hydrogen cation, a catalytically active metal cation, or mixtures thereof. Klotz also discloses that the original cation "M" in the above formulation can be replaced by tetraalkylammonium cations, metal ions, ammonium ions, hydrogen ions, and mixtures thereof, particularly hydrogen, rare earth metals, aluminum, metals of Groups IB, IIB and VIII of the Periodic Table, noble metals, manganese, and other catalytically-active materials and metals known to the art. The catalytically-active components can be present at concentrations from about 0.05 to about 25 weight percent of the crystalline borosilicate. Klotz discloses that the crystalline borosilicate can be employed effectively as a catalyst for various processes including reforming, hydrocracking, transalkylation, disproportionation, isomerization, and alkylation, and is particularly suitable for the isomerization of xylenes, the conversion of ethylbenzene and the conversion of alcohols, such as methanol, to useful products, such as aromatics or olefins.

Fraenkel et al., U.S. Pat. No. 4,294,725 disclose a Fischer-Tropsch catalyst comprising a particulate synthetic zeolite incorporating a transition metal reduced in situ by a preselected vaporous reductant metal and a method of making the catalyst. In the disclosed method for making the catalyst, at least one reducible transition metal is incorporated by ion exchange into a particulate synthetic zeolite catalyst support having ion-exchange properties, and the transition metal is then reduced with a vapor of at least one reductant metal having a reduction potential greater than the reduction potential of the transition metal. In one specific embodiment disclosed, cadmium is disclosed as a reducing metal which is present along with a transition metal in the final catalyst produced. Depending upon the conditions employed, saturated and unsaturated hydrocarbon products containing from one to five carbon atoms and an unidentified oxygenated product were produced when a catalyst containing cobalt as the transition metal and cadmium at the reducing metal was employed.

Chu, U.S. Pat. No. 4,384,155, discloses a process for the conversion of aromatic compounds, either alone or in admixture with a suitable alkylating agent, such as methanol or ethylene, to dialkylbenzene compounds which are rich in the 1,4-dialkylbenzene isomer, in the presence of a particular type of zeolite catalyst having a silica-to-alumina mole ratio of at least 12 and a constraint index of about 1–12, and containing a minor proportion of cadmium deposited thereon.

In addition, cadmium-containing catalysts have been employed in other unrelated methods. For example, Wietzel et al., U.S. Pat. No. 1,562,480, disclose a method for synthesizing higher molecular weight organic compounds containing oxygen by reacting an aliphatic alcohol with carbon monoxide and optionally with hydrogen at a temperature of at least about 400° C. and in the presence of the catalyst comprising both hydrogenating and hydrating constituents. Suitable hydrogenating constituents are disclosed as including copper, silver, gold, tin, lead, antimony, bismuth, zinc, cadmium and thallium, and suitable hydrating constituents are disclosed as including titanium, zirconium, thorium, vanadium, niobium, manganese, cerium, lanthanum, tantalum, chromium, molybdenum, tungsten, uranium, didymium, glucinium and aluminum.

Perkins et al., U.S. Pat. No. 2,107,710, disclose a method for hydrolyzing a halohydrocarbon in the vapor phase and in the presence of a catalyst comprising silica gell impregnated with one or more salts of metals belonging to the Groups IIB, IIIB, IVA or B, or VB of the periodic system, for example, beryllium nitrate, magnesium sulfate, zinc sulfate, cadmium nitrate, boron fluoride, aluminum chloride, stannous chloride, lead nitrate, titanium tetrachloride, antimony nitrate or bismuth chloride.

La Lande, U.S. Pat. No. 2,395,931, discloses a decolorizing adsorbent or catalyst comprising a water-insoluble metal aluminate formed by the reaction in aqueous solution of an alkali metal aluminate and a water-soluble salt of a metal capable of forming a water-insoluble metal aluminate in the presence of a compound yielding ammonium ions. Suitable water-soluble salts of metals capable of forming a water-insoluble metal aluminate include the chlorides or sulfates of magnesium, calcium, or aluminum, and soluble salts of strontium, barium, lead, copper, cadmium, iron, chromium, cobalt, nickel, manganese, thorium, cerium, beryllium, molybdenum, tin, titanium, zirconium, tungsten and vanadium. The catalyst is disclosed for use in decolorizing hydrocarbon oils.

Mecorney et al., U.S. Pat. No. 2,697,730, disclose a catalyst comprising one or more metals, such as copper, silver, chromium, manganese, nickel, tungsten, cobalt, iron, cadmium, uranium, thorium, tin or zinc, either in the form of the elemental metals, their oxides, hydroxides, or salts, wherein the metal component is supported on activated alumina or diatomaceous earth. The catalyst is disclosed for use in synthesizing higher ketones.

Cislak et al., U.S. Pat. No. 2,744,904, disclose a process for preparing pyridine and 3-picoline by reacting acetylene, ammonia and methanol in the presence of a catalyst comprising activated alumina impregnated with cadmium fluoride.

Finch et. al., U.S. Pat. No. 2,763,696, disclose a method for reducing alpha- or beta-olefinic aldehydes or ketones to the corresponding alpha- or beta-unsaturated alcohols by direct hydrogenation of the aldehydes or ketones in the vapor phase and in the presence of a catalyst comprising elemental cadmium, its oxide, or a mixture thereof, and one or more additional metals known to have hydrogenating-dehydrogenating characteristics, such as a heavy metal selected from the first, second, sixth or eighth groups of the Periodic Table of the Elements. These metal components of the catalyst are disclosed as being employed either in the unsupported state or as supported on a suitable carrier, such as silica, alumina, kieselguhr or other diatomaceous earth material, pumice or the like.

Pearson et al., U.S. Pat. No. 3,725,531, disclose a process wherein industrial off-gases containing organic sulfur components are contacted with an alumina base catalyst to convert these organic sulfur components to easily removable compounds, such as carbon dioxide and elemental sulfur. The catalyst employed comprises an alumina base support in combination with at least one metal selected from strontium, calcium, magnesium, zinc, cadmium, barium and molybdenum.

Eurlings et al., U.S. Pat. No. 3,862,055, disclose a method for the preparation of a catalyst system having a catalytically-active component of an oxide, metal or alloy of any one or more of copper, zinc, cadmium, nickel, cobalt, iron, manganese or magnesium, homogeneously dispersed over a solid particulate inorganic thermostable carrier material. Suitable inorganic thermostable materials, for use as the carrier, are disclosed generally as including synthetic or mineral carrier materials, such as alumina or silica. Eberly, U.S. Pat. No. 4,358,297, discloses a process wherein a particulate sorbent mass of zeolite, which has been ion-exchanged with zinc or cadmium to provide pore size openings of at least about 5 anstroms, is contacted with a moist hydrocarbon process stream which contains sulfur, sulfur compounds, and other contaminants, these being adsorbed onto the particulate sorbent mass.

Mathe et al., U.S. Pat. No. 4,361,500, discloses a process for the preparation of a supported metal catalyst containing at least one metal belonging to Group A and optionally at least one metal belonging to Group B, where Group A encompasses palladium, rhodium, ruthenium, platinum, iridium, osmium, silver, gold and cadmium, and Group B encompasses zinc, mercury, germanium, tin, antimony and lead. This patent discloses that any of the known substances commonly used as supports for catalysts can be used as a support in the catalyst disclosed, and the following supports are specifically mentioned: activated carbons, aluminum oxides, silicon dioxides, aluminosilicates and various molecular sieves, and barium sulfate. The catalyst is disclosed for use in hydrogenation reactions.

OBJECTS OF THE INVENTION

It is a general object of the present invention to provide a method for the direct production of gasoline boiling range aliphatic compounds and aromatic compounds from less valuable materials.

More particularly, it is an object of the present invention to provide a single-step method for the direct production of branched aliphatic hydrocarbons which boil in the gasoline range.

It is another object of the present invention to provide a single-step method for the direct production of aromatic compounds.

It is a related object of the present invention to provide a single-step method for the direct production of gasoline boiling range aliphatic compounds and aromatic compounds from less valuable materials employing a catalyst having improved activity maintenance.

Other objects and advantages of the invention will become apparent upon reading the following detailed description and appended claims.

SUMMARY OF THE INVENTION

The present invention is a method for reacting hydrogen with at least one of an alcohol containing from 1 to 6 carbon atoms and an olefin containing from 2 to 6 carbon atoms, at a temperature in the range of from about 300° C. to about 480° C., at a pressure in the range of From about 5 to about 150 kilograms per square centimeter, and in the presence of a catalyst composition comprising a cadmium component and a support material having acidic properites. The cadmium component is in the form of the elemental metal, its oxide or salt or a combination thereof, and wherein the cadmium component is present at a concentration level in the range of from about 0.1 to about 20 weight percent, calculated as cadmium oxide and based on the weight of the catalyst.

DETAILED DESCRIPTION

Catalysts suitable for use in the method of this invention comprise a cadmium component and a support material having acidic properties. The cadmium component can be present either as a component deposited on the support or as a component formed from cadmium ions exchanged into the support replacing exchangeable cations in the support. The cadmium component is in the form of elemental cadmium, its oxide or salt or a combination thereof, and is present at a concentration level in the range of from about 0.1 to about 20 weight percent, calculated as cadmium oxide and based on the weight of the catalyst. Preferably the cadmium component is present at a concentration level of from about 1 to about 10 weight percent, calculated as cadmium oxide and based on the weight of the catalyst. The cadmium component if preferably in the form of cadmium oxide.

Preferably the catalyst additionally comprises a thorium component. The thorium component has essentially no catalytic activity itself in the method of this invention, but serves to promote the catalytic activity of the cadmium component. Like the cadmium component, the thorium component can be present either as a component deposited on the support or as a component of the support formed from thorium ions exchanged into the support replacing exchangeable cations in the support. In addition, a thorium component can be a component of the support formed by admixture of a thorium component with an amorphous refractory inorganic oxide, such as alumina, silica or silica-alumina. The thorium component is in the form of elemental thorium, its oxide or salt or a combination thereof, and is present at a concentration level in the range of from about 1 to about 25 weight percent, calculated as thorium oxide and based on the weight of the catalyst. Preferably, the thorium component is present at a concentration level of from about 3 to about 15 weight percent, calculated as thorium oxide and based on the weight of the catalyst. The thorium component is preferably in the form of thorium oxide.

Any porous support material having acidic properties is suitable for use in the catalyst employed in the method of this invention. Thus, suitable supports comprise an amorphous refractory inorganic oxide, a molecular sieve, a pillared smectite or vermiculite clay, or a combination thereof. Refractory inorganic oxides having acidic properties typically comprise alumina, zirconia, titania, an oxide of a metal of the lanthanide series, an oxide of a metal of the actinide series, a combination thereof, or a combination thereof with silica or magnesia. The amorphous refractory inorganic oxide can also include adjuvants, such as one or more oxides of phosphorus or boron, or a halogen, such as chlorine or fluorine.

The support material of the catalyst employed in the method of the present invention can also comprise a crystalline molecular sieve containing exchangeable cations and can be in the unexchanged or cation-exchanged form. A suitable molecular sieve comprises a crystalline aluminosilicate, crystalline borosilicate or a combination thereof. A suitable crystalline aluminosilicate includes chabazite, clinoptilolite, erionite, mordenite, zeolite A, zeolite L, zeolite X, zeolite Y, ultrastable large-pore zeolite Y, zeolite omega, or a ZSM-type zeolite such as ZSM-5, ZSM-11, ZSM-12, ZSM-35, ZSM-38 or ZSM-48.

Mordenite-type crystalline aluminosilicates have been discussed in the patent art, for example, in Kimberlin, U.S. Pat. No. 3,247,098; Benesi et al., U.S. Pat. No. 3,281,483; and Adams et al., in U.S. Pat. No. 3,299,153. Those portions of each of these patents that are directed to mordenite-type aluminosilicates are specifically incorporated by reference herein. Synthetic mordenite-type crystalline aluminosilicates, designated as Zeolon, are available from the Norton Company of Worcester, Massachusetts.

One example of a crystalline molecular sieve that is suitable for use in the support of the catalyst employed in method of the present invention is an unexchanged high sodium content, Y-type zeolitic crystalline alumino-silicate, such as the sodium-Y molecular sieve, designated as Catalyst Base 30-200, and obtained from the Linde Division of Union Carbide Corporation.

Another example of a crystalline molecular sieve that can be employed in the support of the catalyst employed in the method of the present invention is a metal-exchanged, Y-type molecular sieve. Y-type, zeolitic molecular sieves are discussed in U.S. Pat. No. 3,130,007. The metal-exchanged, Y-type molecular sieve can be prepared by replacing the original cation associated with the molecular sieve by a wide variety of other cations according to techniques that are known in the art. Ion exchange techniques have been disclosed in many patents, several of which are U.S. Pat. Nos. 3,140,249; 3,140,251; and 3,140,253. Specifically, a mixture of rare earth metals can be exchanged into a Y-type zeolitic molecular sieve, and such rare earth metal-exchanged, Y-type molecular sieve can be employed suitably in a support used in the catalyst employed in the method of the present invention. Specific examples of suitable rare earth metals are cerium, lanthanum, and praesodymium. In one particularly preferred embodiment, cadmium ions are exchanged into a Y-type zeolitic molecular sieve, with the result being that the cadmium component of the catalyst is a component of the catalyst support.

Ultrastable, large-pore, Y-type, zeolitic crystalline aluminosilicate material is described in U.S. Pat. Nos. 3,293,192 and 3,449,070. Each of these patents is specifically incorporated by reference herein. By large-pore material is meant, a material that has pores which are sufficiently large to permit the passage thereinto of benzene molecules and larger molecules and the passage therefrom of reaction products.

The ultrastable, large-pore, Y-type, zeolitic crystalline aluminosilicate material that is preferred for use in the support of the catalyst employed in the method of this invention exhibits a cubic unit cell dimension and hydroxyl infrared bands that distinguish it from other aluminosilicate materials. The cubic unit cell dimension of the preferred ultrastable, large-pore, crystalline aluminosilicate is within the range of about 24.20 angstroms to about 24.55 angstroms. The hydroxyl infrared bands obtained with the preferred ultrastable, large-pore, crystalline aluminosilicate material are a band near 3,745 cm$^{-1}$ (3,745±5 cm$^{-1}$), a band near 3,695 cm$^{-1}$ (3,690±10 cm$^{-1}$), and a band near 3,625 cm$^{-1}$ (3,610±15 cm$^{-1}$). The band near 3,745 cm$^{-1}$ may be found on many of the hydrogen-form and de-cationized aluminosilicate materials, but the band near 3,695 cm$^{-1}$ and the band near 3,625 cm$^{-1}$ are characteristic of the preferred ultrastable, large-pore, Y-type, zeolitic crystalline aluminosilicate material that is used in the catalyst of the present invention. The ultrastable, large-pore, Y-type, zeolitic crystalline aluminosilicate material is also characterized by an alkaline metal content of less than 1%.

Other molecular sieve materials that are useful in the support of the catalyst employed in the method of the present invention are ZSM-type crystalline aluminosilicate molecular sieves. Suitable crystalline aluminosilicates of this type typically have silica-to-alumina mole ratios of at least about 12:1 and pore diameters of at least 5 angstroms. A specific example of a useful crystalline aluminosilicate zeolite of the ZSM-type is ZSM-5, which is described in detail in U.S. Pat. No. 3,702,886. Other crystalline aluminosilicate zeolites of the ZSM-type contemplated according to the invention include, ZSM-11, which is described in detail in U.S. Pat. No. 3,709,979; ZSM-12, which is described in detail in U.S. Pat. No. 3,832,449; ZSM-35, which is described in U.S. Pat. No. 4,016,245; and ZSM-38, which is described in detail in U.S. Pat. No. 4,046,859. All of the aforesaid patents are incorporated herein by reference. A preferred crystalline aluminosilicate zeolite of the ZSM-type is ZSM-5.

An additional molecular sieve that can be used in the catalytic composition of the present invention is a crystalline borosilicate, which is described in U.S. Pat. No. 4,269,813, which patent is specifically incorporated herein by reference. A suitable crystalline borosilicate is a molecular sieve material having the following composition in terms of mole ratios of oxides:

$$0.9 +/- 0.2\ M_{2/n}O: B_2O_3: ySiO_2: zH_2O$$

wherein M is at least one cation having a valence of n, y is within the range of 4 to about 600, and z is within the range of 0 to about 160, and providing an X-ray pattern providing the following X-ray diffraction lines and assigned strengths:

| d Angstroms | Assigned Strength |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

N can be a cadmium ion, and thus the cadmium component can be incorporated into the crystalline borosilicate molecular sieve support itself, in addition to or instead of being deposited on the surface of the crystalline borosilicate molecular sieve support.

Suitable methods for preparing the aforesaid crystalline borosilicate molecular sieve are disclosed in Klotz, U.S. Pat. No. 4,269,813 and in Haddid, European patent application No. 82303246.1 which was published on Jan. 5, 1983.

Pillared smectite and vermiculite clays, which are also suitable for use in, or as, the support component of the catalyst employed in the method of this invention, are often referred in the literatue as pillared interlayered clays and occasionally as molecular sieves. The smectite clays comprise montmorillonite, beidellite, montronite, volchonskoite, hectorite, saponite, stevensite, sauconite and pimelite. Some pillared smectite and vermiculite clay materials that are suitable for use in the support of the catalyst employed in the method of this invention, and methods for preparing such clays, are disclosed in Vaughan et al., U.S. Pat. No. 4,176,090; Shabria et al., U.S. Pat. No. 4,216,188; Shabtai, U.S. Pat. No. 4,238,364; D'Aniello, U.S. Pat. No. 4,380,510; Pinnavaia, "Intercalated Clay Catalysts," Science, Vol. 220, pages 365–371 (Apr. 22, 1983) and Vaughan et al., "Preparation of Molecular Sieves Based on Pillared Interlayered Clays (PILC)," Fifth International Conference on Zeolites, pages 94–101 and in the references cited therein. Preferably, a suitable pillared smectite or vermiculite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

Preferably, when the support comprises an aforesaid molecular sieve material or an aforesaid pillared smectite or vermiculite clay material or a combination thereof, the support also comprises an aforesaid amorphous refractory inorganic oxide. In such cases, the concentrations of the amorphous inorganic oxide and of the molecular sieve material and/or pillared smectite or vermiculite clay material are not critical. Preferably, the amorphous refractory inorganic oxide content is at least high enough to be effective to give the support sufficient strength and integrity so that the ultimate catalyst composition can be employed in the method of the present invention without appreciable damage to the catalyst. In such case, the total concentration of the molecular sieve material and/or pillared smectite or vermiculite clay material in such mixture is preferably from 5 to 90 weight percent, more preferably from 20 to 60 weight percent, based on the weight of the support, which support is made up of the amorphous refractory inorganic oxide and the molecular sieve material and/or the pillared smectite or vermiculite clay material.

Preferably, when the support comprises a mixture of a molecular sieve and/or pillared smectite or vermiculite clay and an amorphous refractory inorganic oxide, the support is in the form of a dispersion of the molecular sieve component and/or pillared smectite or vermiculite clay component in a matrix of the amorphous refractory inorganic oxide. Such dispersions can be prepared by well-known techniques, such as blending the molecular sieve component and/or pillared smectite or vermiculite clay component, preferably in finely-divided form, into a sol, hydrosol or hydrogel of the inorganic oxide, and then adding a gelling medium, such as ammonium hydroxide, and stirring to produce a gel. Alternately, the molecular sieve component and/or pillared smectite or vermiculite clay component is blended into a slurry of the amorphous inorganic oxide. In either case, the resulting mixture can be dried, shaped, if desired, and then calcined to form the final support component. A less preferred, but still suitable, method for preparing a suitable dispersion of the molecular sieve component and/or pillared smectite or vermiculite clay component in the inorganic oxide is to dry-blend particles of each, preferably in finely-divided form, and then to conduct any desired shaping operations, such as pelletizing or extrusion; the resulting mixture is then calcined.

The catalysts employed in the method of this invention can be prepared by impregnation of an aforesaid suitable support with at least one precursor of the cadmium component and optionally of the thorium component. Any convenient conventional impregnation technique can be employed for this purpose. For example, when the support comprises an amorphous refractory inorganic oxide, a soluble cadmium compound and, if a thorium component is to be present, a soluble thorium compound can be added to a sol or gel of the amorphous refractory inorganic oxide. This composition is thoroughly blended, and the sol or gel mixture is subsequently co-gelled by the addition of a dilute ammonia solution. The resulting co-gelled material is then dried and calcined. In another method of preparation, the refractory inorganic oxide is gelled, dried, calcined, and cooled, and the resulting material is then impregnated with one or more solutions of a cadmium compound and, if a thorium component is to be present, of a thorium compound.

When the support comprises both an amorphous refractory inorganic oxide and a molecular sieve and/or a pillared smectite or vermiculite clay, numerous convenient impregnation techniques can also be employed. For example, finely-divided molecular sieve material and/or pillared smectite or vermiculite clay material can be stirred into a sol or gel of a refractory inorganic oxide, and at least one soluble compound of cadmium—and optionally at least one soluble compound of thorium—is added to the sol or gel, followed by co-gelling of the sol or gel mixture by the addition of dilute ammonia.

The resulting co-gelled material is then dried and calcined.

In another method of preparation, finely-divided molecular sieve material and/or pillared smectite or vermiculite clay material are mixed into a sol or gel of a refractory inorganic oxide; the sol or gel mixture is co-gelled by the addition of dilute ammonia and the resulting gel is subsequently dried, calcined, cooled, and then impregnated with a solution or solutions of at least one soluble compound of cadmium and optionally of thorium. As an alternate method of preparation, a hydrogel of a refractory inorganic oxide is blended with finely-divided molecular sieve material and/or pillared smectite or vermiculite clay, and a solution or solutions of at least one soluble compound of cadmium and, optionally, of thorium is added to this blend, and the resulting mixture is thoroughly blended. The blended mixture is then dried and calcined.

In still another method of preparation, the molecular sieve material and/or pillared smectite or vermiculite clay material can be pulverized into a finely-divided state and then physically admixed with a finely-divided powder of the selected refractory inorganic oxide component. After a thorough blending of the solid components, the resulting mixture can be co-pelleted, and impregnated with one or more solutions of a cadmium compound and, optionally, of a thorium compound.

It is, of course, also suitable to impregnate only one of the amorphous refractory inorganic oxide, the molecular sieve material or pillared smectite or vermiculite clay material in the mixture, or to impregnate each of the aforesaid amorphous inorganic oxide, molecular sieve material and/or pillared smectite or vermiculite clay material separately, and then to blend the inorganic oxide and molecular sieve material and/or pillared smectite or vermiculite clay material. Thus, it is contemplated that, if the catalyst employed in the method of this invention comprises an amorphous refractory inorganic oxide and at least one of a molecular sieve material and a pillared smectite or vermiculite clay material, the cadmium component can be deposited on only one, only two, or all of the components of the support. Similarly, in such cases, if a thorium component is also present in the catalyst employed in the method of this invention, the thorium component can be present with the cadmium component on the same component(s) of the support, or the cadmium component and thorium component can be on different components of the support.

It is preferred that, if the catalyst employed in the method of this invention comprises a support comprising a molecular sieve component or a pillared smectite or vermiculite clay component impregnated with the cadmium component and/or the thorium component, the impregnation of the molecular sieve component and pillared smectite or vermiculite clay component is conducted at a pH of at least about 2 in order to avoid substantial destruction of the crystallinity of the aforesaid support component. More preferably, the pH of the impregnating solution(s) in such case is from about 2.5 to about 6 in order to ensure substantial retention of the crystallinity of the aforesaid support component. Of course, the optimum pH range(s) of the impregnating solution(s) varies somewhat depending on the specific molecular sieve component and pillared smectite or vermiculite clay component employed in the preparation of a given catalyst.

In each of the above preparations involving a molecular sieve material, the molecular sieve material employed can be either in its unexchanged form or in its ion-exchanged form. Preferably, the molecular sieve material is one which has previously been cation-exchanged. A suitable cation-exchange procedure comprises making a slurry of the molecular sieve material in a solution of a cation, such as ammonium ions, which is to be exchanged with the alkali metal in the molecular sieve material, stirring the slurry at a temperature of about 100° C. for at least about 2 hours to about one week, filtering the slurry, washing the filtered solid with distilled water, and drying and calcining the solid.

It is also suitable to incorporate the precursor of the cadmium component into the molecular sieve by cation exchange using a convenient, conventional ion exchange procedure, such as the one described generally hereinabove. Thus, the cadmium component can be incorporated into the molecular sieve support itself, in addition to or instead of being deposited on the surface of the molecular sieve support.

Suitable conditions for drying the above-described cadmium-impregnated or cadmium-exchanged supports comprise a temperature in the range of from about 90° C. to about 200° C. and a drying time of from about 0.5 to about 30 hours. Suitable calcination conditions in such methods comprise a temperature in the range of about 480° C. to about 760° C. and a calcination time of from about 2 to about 5 hours. Preferred drying and calcination conditions are a temperature of about 120° C. for about 1–2 hours and a temperature of about 538° C. for about 1–2 hours, respectively.

The general method of this invention comprises reacting hydrogen with at least one of an alcohol containing from 1 to 6 carbon atoms and an olefin containing from 2 to 6 carbon atoms, in the presence of an aforesaid catalyst suitable for use in the method of this invention. The conditions employed in the method of this invention include a temperature in the range of from about 300° C. to about 480° C. and a pressure in the range of from about 5 to about 150 kilograms per square centimeter.

The alcohol employed in the method of this invention preferably comprises methanol, ethanol, propanol or a combination thereof. When an alcohol is not a reactant, the olefin employed in the method of this invention preferably comprises propylene, butylene, amylene or a combination thereof. When an alcohol is a reactant, the olefin preferably comprises ethylene, propylene, butylene or a combination thereof. If an alcohol is a reactant, the mole ratio of alcohol-to-hydrogen is preferably from about 1:10 to about 10:1, more preferably from about 4:1 to about 1:4. If an olefin is a reactant, the mole ratio of olefin-to-hydrogen is preferably from about 10:1 to about 1:10, more preferably from about 4:1 to about 1:1. If both an alcohol and an olefin are reactants, the mole ratio of alcohol-to-olefin is preferably from about 10:1 to about 1:10, more preferably from about 3:1 to about 1:3. In such cases, it is also preferred that the reaction is performed at a temperature in the range of from about 315° C. to about 425° C., at a pressure of at least about 10 kilograms per square centimeter, and with a space velocity of from about 0.01 to about 0.1 moles of each of the alcohol and olefin that is present per gram of catalyst per hour. In addition, the reaction between hydrogen and at least one of the alcohol and olefin, when an alcohol is present, is preferably performed in the presence of a catalyst comprising a support comprising cadmium-exchanged zeolite Y, rare earth-exchanged zeolite Y, ultrastable zeolite Y, a pillared smectite or vermiculite clay, silica-alumina, crystalline borosilicate molecular sieve, or ZSM-5, and more preferably the catalyst additionally comprises a thorium component and the support comprises silica-alumina. Preferably, when an alcohol is not present, such catalyst comprises a support comprising cadmium-exchanged zeolite Y, rare earth-exchanged zeolite Y, ultrastable zeolite Y, crystalline borosilicate molecular sieve, or ZSM-5.

The present invention will be more clearly understood from the following specific examples.

EXAMPLE 1

A solution containing 3 grams of $Cd(NO_3)_2.4H_2O$ in 14 milliliters of water was combined and blended for 1 hour with 23.75 grams of gamma alumina (from Continental Oil Company and designated Catapal) having a pore volume of 0.65 cubic centimeter per gram, a surface area of 200 square meters per gram, an average pore diameter of 130 angstroms, and a particle size of 0.16 centimeter. The blend was then dried at 120° C. for 1 hour and calcined at 540° C. in air for 1 hour. The resulting catalyst contained 5 weight percent of cadmium oxide, based on the weight of the catalyst.

EXAMPLE 2

The procedure of Example 1 was repeated except that a solution containing 3 grams of $Cd(NO_3)_2.4H_2O$ and 7.84 grams of $Th(NO_3)_4.4H_2O$ in 9 milliliters of water was combined and blended with the alumina. The resulting catalyst contained 5 weight percent of cadmium oxide and 15 weight percent of thorium oxide, based on the weight of the catalyst.

EXAMPLE 3

35.4 grams of $Th(NO_3)_4.4H_2O$ was dissolved in water and blended with 555.7 grams of an alumina sol containing about 9 weight percent of alumina. 25 milliliters of an aqueous solution containing about 28 weight percent of ammonium hydroxide was added to the resulting blend to gel the sol. The resulting gel was dried at 120° C. overnight and then calcined at 540° C. in air for 4 hours. The resulting composite material contained 25 weight percent of thorium oxide. A solution containing 6 grams of $Cd(NO_3)_2.4H_2O$ in 10 milliliters of water was then blended with 18 grams of the composite and the procedure of Example 1 was followed. The resulting catalyst contained 10 weight percent of cadmium oxide and 22.5 weight percent of thorium oxide, based on the weight of the catalyst.

EXAMPLE 4

691 grams of an alumina sol containing about 10 weight percent of alumina was blended with 3000 grams of a silica-alumina sol containing about 5.24 weight percent of silica-alumina of which about 72 weight percent was silica and about 28 weight percent was alumina. 400 milliliters of an aqueous solution containing about 50 weight percent of ammonium hydroxide was blended with the aforesaid blend until a pasty consistency was achieved.

This procedure was repeated twice so that 3 batches of the paste were collected. The 3 batches were then combined, and 1 liter of the aforesaid aqueous ammonium hydroxide solution was added to the resulting combination. After standing for 24 hours, the resulting mixture was dried in air at 120° C. for several days, ground and sieved to pass a 100 mesh sieve (U.S. Series). The resulting solid was mulled with water and a small amount of PHF alumina, and was then extruded to a diameter of 0.16 centimeter. The extrudate was dried overnight in air at 120° C. and then calcined in air at 538° C. for 4 hours. The resulting material contained 50 weight percent of alumina and 50 weight percent of silica, and had a pore volume of 0.48 cubic centimeter per gram, a surface area of 227 square meters per gram and an average pore diameter of 110Å.

The procedure of Example 1 was then repeated except that a solution containing 10.82 grams of $Cd(NO_3)_2.4H_2O$ in 41 milliliters of water was blended with 45.5 grams of the resulting silica-alumina containing 50 weight percent of silica and 50 weight percent of alumina. The resulting catalyst contained 9 weight percent of cadmium oxide, based on the weight of the catalyst.

EXAMPLE 5

The procedure of Example 4 was repeated, except that a solution containing 5.4 grams of $Cd(NO_3)_2.4H_2O$ and 7.84 grams of $Th(NO_3)_2.4H_2O$ was blended with 19 grams of the type of the silica-alumina composite containing 50 weight percent of silica and 50 weight percent of alumina and used in Example 4. The resulting catalyst contained 9 weight percent of cadmium oxide and 15 weight percent of thorium oxide, based on the weight of the catalyst.

EXAMPLE 6

The procedure of Example 4 was repeated, except that a solution containing 3 grams of $Cd(NO_3)_2.4H_2O$ and 6.27 grams of $Th(NO_3)_2.4H_2O$ was blended with 16 grams of the type of the silica-alumina composite containing 50 weight percent of silica and 50 weight percent of alumina and used in Example 4. The resulting catalyst contained 5 weight percent of cadmium oxide and 15 weight percent of thorium oxide, based on the weight of the catalyst.

EXAMPLE 7

300 grams of zeolite Y in the sodium form (from Union Carbide Corporation and designated LZ-Y52) was slurried in 8 liters of water, and 4000 grams of a solution of a commercially available mixture of rare earth chlorides was added to the slurry. The resulting slurry was stirred and heated at reflux for 1 hour. The solids were allowed to settle overnight and the supernatant liquid was siphoned off. The resulting solids were exchanged a second time with 4 kilograms of the mixture of rare earth chlorides in 2 liters of water, and the aforesaid stirring, refluxing, settling and siphoning steps were repeated. The resulting solids were exchanged a third time with 4 kilograms of the mixture of rare earth chlorides in 6 liters of water, and the aforesaid stirring, refluxing, settling and siphoning steps were repeated. The resulting solids were washed each of 4 times with 6 liters of water, dried overnight at 120° C. and calcined for 4 hours at about 780° C.

The aforesaid triple exchange was repeated, except using instead in each exchange solution 2000 grams of the mixture of rare earth chlorides and additionally in the third exchange solution 400 grams of ammonium nitrate. The stirring, refluxing, settling, siphoning, washing and drying steps were as described for the first triple exchange.

The aforesaid triple exchange was repeated a second time, using the same steps and conditions employed in the aforesaid second triple exchange.

The final rare earth-exchanged zeolite Y demonstrated 92 percent crystallinity and contained 0.241 weight percent of sodium, 2.4 weight percent of lanthanum, 8.6 weight percent of cerium, 2.9 weight percent of neodymium, 0.20 weight percent of thorium, 1.1 weight percent of yttrium, 6.6 weight percent of aluminum and 24.8 weight percent of silicon.

120.0 grams of the resulting rare earth-exchanged zeolite Y was ground to pass a 100 mesh sieve (U.S. Series) and mixed with approximately 400 milliliters of water. The resulting mixture was blended with 2800 grams of an alumina sol containing about 10 weight percent of alumina. 300 milliliters of an aqueous solution of ammonium hydroxide containing 50 weight percent of ammonium hydroxide was added rapidly to the resulting blend, with stirring, to gel the mixture of the rare earth-exchanged zeolite Y and alumina. The gelled material was dried at 120° C. for 40 hours. The dried material was then ground to pass a 100 mesh sieve (U.S. Series), mulled with water and extruded to a diameter of 0.2 centimeter. The extrudate was dried at 120° C. in air for 6 hours and then calcined at 540° C. in air for 6 hours. The resulting composition contained 30 weight percent of rare earth-exchanged zeolite Y and 70 weight percent of alumina.

EXAMPLE 8

A solution containing 1.91 grams of $Cd(NO_3)_2.4H_2O$ in 6.5 milliliters of water was combined and blended for 1 hour with 15.1 grams of the final rare earth-exchanged zeolite Y produced in Example 7. The blend was then dried at 120° C. for 1 hour and calcined at 540° C. in air for 1 hour. The resulting catalyst contained 5 weight percent of cadmium oxide, based on the weight of the catalyst.

EXAMPLE 9

A solution containing 3 grams of $Cd(NO_3)_2.4H_2O$ and 7.84 grams of $Th(NO_3)_4.4H_2O$ in 8 milliliters of water was combined and blended for 1 hour with 20 grams of the final rare earth-exchanged zeolite Y produced in Example 7. The blend was then dried at 120° C. for 1 hour and calcined at 540° C. in air for 1 hour. The resulting catalyst contained 5 weight percent of cadmium oxide and 15 weight percent of thorium oxide, based on the weight of the catalyst.

EXAMPLE 10

A solution containing 12 grams of $Cd(NO_3)_2.4H_2O$ in 7 milliliters of water was combined and blended for 1 hour with 20 grams of the final rare earth-exchanged zeolite Y produced in Example 7. The blend was then dried at 120° C. for 1 hour and calcined at 540° C. in air for 1 hour. The resulting catalyst contained 20 weight percent of cadmium oxide, based on the weight of the catalyst.

EXAMPLE 11

25 grams of rare earth-exchanged zeolite Y prepared as in Example 7 was ground to pass a 100 mesh sieve (U.S. Series) and suspended in water. The resulting suspension was blended with 275 grams of an alumina sol containing about 9 weight percent of alumina. 13 milliliters of an aqueous solution containing 28 weight percent of ammonium hydroxide was then added rapidly, with stirring, to the resulting blend to gel the mixture of the rare earth exchanged zeolite Y and alumina. The resulting gelled material was dried overnight at 120° C. and calcined at 540° C. in air for 1 hour. The resulting composition contained 50 weight percent of rare earth-exchanged zeolite Y and 50 weight percent of alumina.

A solution containing 13.4 grams of $Cd(NO_3)_2.4H_2O$ and 17.5 grams of $Th(NO_3)_4.4H_2O$ in 16 milliliters of water was combined and blended for 1 hour with 44.7 grams of the aforesaid composition containing 50 weight percent of rare earth-exchanged zeolite Y and 50 weight percent of alumina. The blend was then dried at 120° C. for several hours and calcined at 540° C. in air for 4 hours. The resulting catalyst contained 5 weight percent of cadmium oxide and 15 weight percent of thorium oxide, based on the weight of the catalyst.

EXAMPLE 12

90 grams of H-Zeolon (Zeolon 200 from the Norton Company) was ground to pass a 100 mesh sieve (U.S. Series), and the resulting particles were slurried with distilled water. The resulting slurry was blended with 3600 grams of an alumina sol containing about 10 weight percent of alumina. 215 milliliters of an aqueous solution containing about 50 weight percent of ammonium hydroxide was then added to gel the mixture of H-Zeolon and alumina. The resulting gel was dried over a period of several days at 120° C. in air. The dried particles were ground to pass a 100 mesh sieve (U.S. Series), mulled with water and extruded to a diameter of 0.2 centimeter. The extrudate was dried at 120° C. for 2 hours in air and calcined at 540° C. for 7 hours in air. The resulting composition contained 20 weight percent of H-Zeolon and 80 weight percent of alumina.

A solution containing 3 grams of $Cd(NO_3)_2.4H_2O$ and 7.84 grams of $Th(NO_3)_4.4H_2O$ in 8 milliliters of water was combined and blended with 20 grams of the aforesaid composition containing 20 weight percent of H-Zeolon in alumina. The blend was then dried at 120° C. for 1 hour and calcined at 540° C. in air for 1 hour. The resulting catalyst contained 5 weight percent of cadmium oxide and 15 weight percent of thorium oxide, based on the weight of the catalyst.

EXAMPLE 13

180 grams of crystalline borosilicate (obtained from Amoco Chemicals Corporation and designated HAMS-1B) was suspended in sufficient water to form a sauce-like consistency and combined and blended with 3600 grams of an alumina sol containing about 10 weight percent of alumina. 400 milliliters of an aqueous solution containing about 50 weight percent of ammonium hydroxide was added to the blend to gel the mixture of crystalline borosilicate and alumina. The resulting gel was dried at 120° C. in air overnight. The dried particles were ground to pass a 100 mesh sieve (U.S. Series), mulled with water, extruded to a diameter of 0.32 centimeter, dried at 120° C. overnight and calcined at 540° C. in air overnight. The resulting composition contained 40 weight percent of crystalline borosilicate HAMS-1B and 60 weight percent of alumina.

A solution containing 3 grams of $Cd(NO_3)_2.4H_2O$ and 7.84 grams of $Th(NO_3)_4.4H_2O$ in 8 milliliters of water was combined and blended for 1 hour with 20 grams of the aforesaid composition containing 40 weight percent of HAMS-1B. The blend was then dried at 120° C. for 1 hour and calcined at 540° C. in air for 1 hour. The resulting catalyst contained 5 weight percent of cadmium oxide and 15 weight percent of thorium oxide, based on the weight of the catalyst.

EXAMPLE 14

The procedure of Example 13 was repeated except that a solution containing 3 grams of $Cd(NO_3)_2.4H_2O$ in 8 grams of water was combined and blended with 19 grams of the composition containing 40 weight percent of crystalline borosilicate HAMS-1B and 60 weight percent of alumina. The blend was then dried at 120° C. for 1 hour and calcined at 540° C. in air for 1 hour. The resulting catalyst contained 5 weight percent of cadmium oxide, based on the weight of the catalyst.

EXAMPLE 15

ZSM-5 having a mole ratio for silica-to-alumina of 30:1 was prepared by dissolving 208 grams of tetrapropylammonium bromide and 42 grams of sodium aluminate in 400 milliliters of an aqueous solution containing 37.2 grams of sodium hydroxide. Then 1077 grams of Ludox (a silica sol) and sufficient water to bring the total solution volume to 18 liters were blended with the aforesaid aqueous solution. The blend was then heated at about 150° C. for 5 days in an autoclave. Thereafter the solid was washed with hot water 3 times, dried overnight at about 120° C. and then calcined at about 540° C.

350 grams of 30:1 ZSM-5 was ground to pass a 100 mesh sieve (U.S. Series) and then suspended in water. The resulting suspension was combined with 2265.4 grams of an alumina sol containing about 10 weight percent of alumina. 400 milliliters of an aqueous solution containing about 14 weight percent of ammonium hydroxide was added to the resulting mixture to form a gel. The resulting gel was dried at 120° C. in air. The dried material was then ground to pass a 100 mesh sieve (U.S. Series) and extruded to a diameter of 0.32 centimeter. The extrudate was dried at 120° C. and then calcined at 540° C. for 20 hours. The resulting composition contained 60 weight percent of ZSM-5 and 40 weight percent of alumina.

A solution containing 3 grams of $Cd(NO_3)_2.4H_2O$ and 7.84 grams of $Th(NO_3)_4.4H_2O$ in 8 milliliters of water was combined and blended for 1 hour with 20 grams of the aforesaid composition containing 60 weight percent of ZSM-5 and 40 weight percent of alumina. The blend was then dried at 120° C. for 1 hour and calcined at 540° C. in air for 1 hour. The resulting catalyst contained 5 weight percent of cadmium oxide and 15 weight percent of thorium oxide, based on the weight of the catalyst.

EXAMPLE 16

A solution containing 150 grams of $Cd(NO_3)_2.4H_2O$ in 800 milliliters of water was added to approximately 100 grams of zeolite Y (LZ-Y52 from Union Carbide) having exchangeable sodium ions. This mixture was stirred and heated for 2 hours, and then filtered and washed, to thereby exchange cadmium ions for some of the exchangeable sodium ions in the zeolite Y. A second solution containing 150 grams of $Cd(NO_3)_2.4H_2O$ was added to the resulting cadmium-exchanged zeolite Y, and the resulting mixture was then stirred and heated for 2 hours. The resulting mixture was allowed to settle overnight and then filtered. The separated solid zeolite Y containing cadmium ions exchanged for some of the sodium ions originally present, was washed with water.

30 grams of this composition was suspended in water, and the resulting suspension was combined with 768.4 grams of an alumina sol containing about 10 weight percent of alumina. 35 milliliters of an aqueous solution containing about 28 weight percent of ammonim hydroxide was added to gel the mixture. The resulting gel was dried overnight at 120° C. and then calcined at 540° C. for 4 hours. The resulting catalyst contained 30 weight percent of the cadium-exchanged zeolite Y and 70 weight percent of alumina. The cadmium, calculated as cadmium oxide, constituted 5.6 weight percent of the catalyst.

EXAMPLE 17

A solution containing 100 grams of $Cd(NO_3)_2.4H_2O$ in 900 milliliters of water was combined with 100 grams of zeolite omega-5 (obtained from Union Carbide and designated ELZ-ω-5) having exchangeable sodium ions. The resulting mixture was heated for 2 hours at 38° C., with stirring, and then filtered and washed with water, to thereby exchange cadmium ions for some of the exchangeable ions in the zeolite omega-5. A second solution containing 100 grams of $Cd(NO_3)_2.4H_2O$ in 900 milliliters of water was added to the resulting cadmium-exchanged zeolite omega-5, and the resulting mixture was again stirred, heated, allowed to settle and filtered. The final twice-cadmium-exchanged zeolite omega-5 was dried overnight at 120° C.

48.1 grams of this composition was ground to pass a 100 mesh sieve (U.S. Series) and suspended in water. This suspension was mixed with 351.85 grams of an alumina sol containing about 10 weight percent of alumina, and 16 milliliters of an aqueous solution containing about 28 weight percent of ammonium hydroxide was added to gel the mixture of zeolite omega-5 and alumina. The resulting gel was dried at 120° C. overnight and then calcined in air at 540° C. for 6 hours. The resulting catalyst contained 60 weight percent of the cadmium-exchanged zeolite omega-5 and 40 weight percent of alumina.

EXAMPLE 18

100 grams of zeolite L (obtained from Union Carbide and designated ELZ-L) was combined with 900 milliliters of water, and potassium hydroxide was added to the resulting mixture to adjust the pH to approximately 11, The mixture was heated at 38° C. for 1 hour, filtered and washed. The recovered solid was combined with a solution containing 100 grams of $Cd(NO_3)_2.4H_2O$ in 800 milliliters of water, and the resulting mixture was heated and stirred for 2 hours, after which time it was allowed to cool and settle overnight. The resulting once-cadmiumexchanged zeolite L was separated by filtration and washed with water, and then re-suspended in 800 milliliters of water. To this suspension 100 grams of $Cd(NO_3)_2.4H_2O$ was added, and the resulting suspension was heated at 38° C. and stirred for 2 hours. The mixture was then allowed to cool and settle overnight. The resulting twice-cadmium-exchanged zeolite L was separated by filtration, washed with water and then dried overnight at 120° C.

79.87 grams of this composition was ground to pass a 100 mesh sieve (U.S. Series) and suspended in water. The suspension was then combined with 584.5 grams of an alumina sol containing about 10 weight percent of alumina, and 27 milliliters of an aqueous solution containing about 28 weight percent of ammonium hydroxide was added to gel the mixture of zeolite L and alumina. The resulting gel was dried at 120° C. overnight and then calcined at 540° C. for 6 hours. The resulting composition contained 60 weight percent of the cadmium-exchanged zeolite L and 40 weight percent of alumina.

EXAMPLE 19

A suspension of 400 grams of a bentonite, 90 weight percent of which is montmorillonite (supplied by American Colloid Company and designated Volclay 325), in 227 cubic centimeters of water was mixed with 304 grams of a 50 weight percent solution of Reheis alumina Chlorhydrol, and the pH of the resulting suspension was adjusted to 4 with ammonium hydroxide. The suspension was heated at 72° C. for 1 hour and then filtered, and the resulting separated solid was washed with water, dried at 100° C. and calcined at 500° C. for 2 hours. The resulting alumina-expanded smectite clay had a d-spacing of 16.6 angstroms as measured by X-ray diffraction. The spacing between the molecular layers of the montmorillonite was between 6 and 10 angstroms and was stable at a temperature of at least 300° C. in an air atmosphere for at least 2 hours.

30.27 grams of this composition was combined with 221.5 grams of an alumina sol containing about 9 weight percent of alumina, and 10 grams of an aqueous solution containing about 28 weight percent of ammonium hydroxide was added to gel the resulting mixture. The resulting gel was dried at 120° C. and calcined at 540° C. for 6 hours. The resulting composition contained 60 weight percent of the alumina-expanded smectite clay and 40 weight percent of alumina.

A solution containing 2.4 grams of $Cd(NO_3)_2.4H_2O$ in 8 milliliters of water was combined and blended with 19 grams of the aforesaid composition containing 60 weight percent of the alumina-expanded smectite clay and 40 weight percent of alumina. The blend was then dried at 120° C. and calcined at 540° C. for 4 hours. The resulting catalyst contained 5 weight percent of cadmium oxide, based on the weight of the catalyst.

EXAMPLE 20

The procedure of Example 19 was repeated except that a solution containing 5.41 grams of $Cd(NO_3)_2.4H_2O$ in 9 grams of water was combined and blended with 22.75 grams of the composition containing 60 weight percent of the alumina-expanded smectite clay and 40 weight percent of alumina. The blend was then dried at 120° C. and calcined at 540° C. for 4 hours. The resulting catalyst contained 9 weight percent of cadmium oxide, based on the weight of the catalyst.

EXAMPLE 21

90 grams of ultrastable zeolite Y crystalline aluminosilicate was slurried in water, and the slurry was combined and blended with 3600 grams of alumina sol containing about 10 weight percent of alumina. 250 grams of an aqueous solution containing about 28 weight percent of ammonium hydroxide was added to gel the resulting mixture. The resulting gel was dried at 120° C. and then ground to pass a 100 mesh sieve (U.S. Series). The ground material was next mulled with water and extruded to a 0.16 centimeter diameter. The extrudate was dried overnight at 120° C. and calcind at 540° C. for 7 hours. The resulting composition contained 30 weight percent of ultrastable zeolite Y and 70 weight percent of alumina.

A solution containing 3 grams of $Cd(NO_3)_2.4H_2O$ and 7.84 grams of $Th(NO_3)_2.4H_2O$ in 8 grams of water was blended with the aforesaid composition containing ultrastable zeolite Y and alumina. The resulting mixture was dried at 120° C. and then calcined at 540° C. for 1 hour. The resulting catalyst contained 5 weight percent of cadmium oxide and 15 weight percent of thorium oxide, based on the weight of the catalyst.

EXAMPLE 22

360 grams of ultrastable zeolite Y crystalline aluminosilicate was slurried in water, and the slurry was combined and blended with 3600 grams of alumina sol containing about 10 weight percent of alumina. 400 grams of an aqueous solution containing about 28 weight percent of ammonium hydroxide was added to gel the resulting mixture. The resulting gel was dried at 120° C. and then ground to pass a 100 mesh sieve (U.S. Series). The ground material was next mulled with water and extruded to a 0.16 centimeter diameter. The extrudate was dried overnight at 120° C. and calcined at 540° C. for 3 hours. The resulting composition contained 50 weight percent of ultrastable zeolite Y and 50 weight percent of alumina.

A solution containing 2.4 grams of $Cd(NO_3)_2.4H_2O$ in 8 grams of water was blended with the aforesaid composition containing ultrastable zeolite Y and alumina. The resulting mixture was dried at 120° C. and then calcined at 540° C. for 4 hours. The resulting catalyst contained 5 weight percent of cadmium oxide, based on the weight of the catalyst.

EXAMPLES 23-63

Examples 23-63 were performed using a 300-cubic centimeter, back-mixed reactor in which the flow into the reactor of each gaseous and liquid reactant employed was controlled individually. To start a run in each of Examples 23-63, 10 grams of the particular catalyst used was loaded into the reactor, and the reactor was closed. The pressure of the reactor was then raised to the desired level by introducing the gaseous reactant(s) employed. The temperature of the reactor was then raised to the desired level, at which point any liquid reactant(s) employed was then introduced into the reactor where it contacted the catalyst and gaseous reactant(s). Products and unreacted reactants passed continuously out of the reactor.

The catalyst, temperature, pressure and feed rates of each reactant employed in Examples 23-63 are presented in Tables 1-8. The feed rate of each liquid reactant is presented in Tables 1-8 in terms of its liquid hourly space velocity-- that is, the feed rate of the liquid in cubic centimeters per hour divided by the number (10) of grams of catalyst in the reactor. The combined feed rate of the gaseous reactant(s) is presented in Tables 1-8 in terms of the gas weight hourly space velocity-- that is, the combined gaseous feed rate in cubic centimeters per hour divided by weight of catalyst in the reactor. When both carbon monoxide and hydrogen were employed, they were introduced into the reactor at a mole ratio of carbon monoxide-to-hydrogen of 1:2. A mixture of hydrogen and carbon monoxide was employed in Examples 23, 24, 26, 28, 33, 35, 36, 38, 42, 44, 46, 48, 50 and 51. Hydrogen was the only gas employed in Examples 25, 27, 29-32, 34, 37, 39-41, 43, 45, 47, 49, 52-58 and 59-63. Methanol was the liquid feed in Examples 25, 27, 29-32, 34, 37, 39-41, 43, 45, 47, 49, 52, 53, and 59-63. Propylene is the liquid feed in Examples 54, 56 and 57. Both methanol and propylene were the liquid feeds in Examples 55 and 58.

The compositions of the organic products for each of Examples 23-63 are also indicated in Tables 1-8. In Tables 1-8, the concentrations of butylenes are not reported separately but are included in the concentrations of $i-C_5H_{12}$ and $n-C_5H_{12}$. In all of the tables, T indicated trace amounts.

TABLE 1

| Example No. | 23 | 24 | 25 | 26 | 27 |
|---|---|---|---|---|---|
| Catalyst from Example No. | 4 | 4 | 4 | 5 | 6 |
| Temperature (°C.) | 393 | 393 | 413 | 432 | 432 |
| Pressure (atm.) | 34 | 68 | 34 | 34 | 34 |
| Gas feed rate (cc./hr./gm.) | 2000 | 3400 | 700 | 2000 | 900 |
| Liquid feed rate (cc./hr./gm.) | — | — | 1.0 | — | 1.0 |
| Product Composition (Wt. %) | | | | | |
| $CH_4$ | 45 | 38 | 5 | 75 | 7 |
| $C_2H_6$—$C_2H_4$ | 15 | 14 | 12 | 9 | 11 |
| $C_3H_6$ | 3 | 4 | 5 | 4 | 5 |
| $C_3H_8$ | 4 | 3 | 8 | 1 | 8 |
| $i-C_4H_{10}$ | 9 | 10 | 12 | 3 | 9 |
| $n-C_4H_{10}$ | 1 | 2 | 1 | 1 | 2 |
| $i-C_5H_{12}$ | 9 | 9 | 8 | 3 | 6 |
| $n-C_5H_{12}$ | T | T | T | T | t |
| $i-C_6H_{14}$ | 7 | 6 | 5 | 2 | 5 |
| $n-C_6H_{14}$ | T | T | T | T | 1 |
| $C_6+$ | 7 | 14 | 31 | 2 | 30 |
| DME | — | — | 13 | — | 16 |

TABLE 2

| Example No. | 28 | 29 | 30 | 31 | 32 |
|---|---|---|---|---|---|
| Catalyst from Example No. | 21 | 21 | 21 | 21 | 21 |
| Temperature (°C.) | 399 | 399 | 399 | 427 | 456 |
| Pressure (atm.) | 34 | 34 | 68 | 34 | 34 |
| Gas feed rate (cc./hr./gm.) | 1100 | 1400 | 1400 | 1400 | 1400 |
| Liquid feed rate (cc./hr./gm.) | — | 1.0 | 1.0 | 1.0 | 1.0 |
| Product Composition (Wt. %) | | | | | |
| $CH_4$ | 27 | 12 | 27 | 18 | 21 |
| $C_2H_6$—$C_2H_4$ | 6 | 4 | 3 | 7 | 8 |
| $C_3H_8$ | 4 | 3 | 3 | 5 | 5 |
| $C_3H_6$ | 6 | 5 | 3 | 5 | 6 |
| $i-C_4H_{10}$ | 16 | 25 | 18 | 22 | 18 |
| $n-C_4H_{10}$ | 2 | 2 | 2 | 3 | 3 |
| $i-C_5H_{12}$ | 13 | 17 | 18 | 16 | 15 |
| $n-C_5H_{12}$ | 1 | 1 | 1 | 2 | 2 |
| $i-C_6H_{14}$ | 9 | 11 | 6 | 10 | 9 |
| $n-C_6H_{14}$ | 1 | 1 | 1 | 1 | 1 |
| $C_6+$ | 15 | 12 | 12 | 9 | 10 |
| DME | — | 7 | 6 | 2 | 2 |

TABLE 3

| Example No. | 33 | 34 | 35 | 36 | 37 |
|---|---|---|---|---|---|
| Catalyst from Example No. | 8 | 8 | 9 | 9 | 9 |
| Temperature (°C.) | 405 | 399 | 399 | 399 | 371 |
| Pressure (atm.) | 34 | 34 | 68 | 34 | 34 |
| Gas feed rate (cc./hr./gm.) | 600 | 800 | 1700 | 1700 | 1100 |
| Liquid feed rate (cc./hr./gm.) | — | 1.0 | — | — | 1.0 |
| Product Composition (Wt. %) | | | | | |
| $CH_4$ | 24 | 15 | 16 | 12 | 6 |
| $C_2H_6$—$C_2H_4$ | 2 | 2 | 8 | 8 | 3 |
| $C_3H_8$ | 19 | 18 | 5 | 3 | 2 |
| $C_3H_6$ | 1 | 1 | 3 | 5 | 3 |
| $i-C_4H_{10}$ | 27 | 30 | 18 | 17 | 36 |
| $n-C_4H_{10}$ | 6 | 7 | 3 | 2 | 2 |
| $i-C_5H_{12}$ | 10 | 10 | 17 | 13 | 19 |
| $n-C_5H_{12}$ | 1 | 1 | 1 | 1 | 1 |

TABLE 3-continued

| Example No. | 33 | 34 | 35 | 36 | 37 |
|---|---|---|---|---|---|
| $i-C_6H_{14}$ | 5 | 4 | 10 | 9 | 11 |
| $n-C_6H_{14}$ | — | — | — | — | — |
| $C_6+$ | 5 | 11 | 19 | 30 | 15 |
| DME | — | 1 | — | — | 5 |

TABLE 4

| Example No. | 38 | 39 | 40 | 41 |
|---|---|---|---|---|
| Catalyst from Example No. | 19 | 19 | 19 | 19 |
| Temperature (°C.) | 399 | 405 | 432 | 427 |
| Pressure (atm.) | 34 | 34 | 34 | 34 |
| Gas feed rate (cc./hr./gm.) | 2000 | 1800 | 2250 | 4500 |
| Liquid feed rate (cc./hr./gm.) | — | 1.0 | 1.0 | 3.0 |
| Product Composition (Wt. %) | | | | |
| $CH_4$ | 28 | 11 | 18 | 13 |
| $C_2H_6$—$C_2H_4$ | 7 | 5 | 7 | 5 |
| $C_3H_8$ | 11 | 10 | 8 | 2 |
| $C_3H_6$ | 1 | 2 | 4 | 5 |
| $i-C_4H_{10}$ | 19 | 27 | 20 | 9 |
| $n-C_4H_{10}$ | 4 | 5 | 4 | 2 |
| $i-C_5H_{12}$ | 9 | 14 | 12 | 6 |
| $n-C_5H_{12}$ | 1 | 1 | 1 | 1 |
| $i-C_6H_{14}$ | 5 | 8 | 8 | 6 |
| $n-C_6H_{14}$ | 1 | 0 | 0 | 0 |
| $C_6+$ | 14 | 15 | 15 | 14 |
| DME | — | 2 | 3 | 36 |

TABLE 5

| Example No. | 42 | 43 | 44 | 45 |
|---|---|---|---|---|
| Catalyst from Example No. | 13 | 13 | 15 | 15 |
| Temperature (°C.) | 399 | 399 | 399 | 399 |
| Pressure (atm.) | 34 | 34 | 34 | 34 |
| Gas feed rate (cc./hr./gm.) | 1850 | 1400 | 2000 | 1400 |
| Liquid feed rate (cc./hr./gm.) | —* | 1.0 | — | 1.0 |
| Product Composition (Wt. %) | | | | |
| $CH_4$ | 88 | 20 | 85 | 23 |
| $C_2H_6$—$C_2H_4$ | 10 | 2 | 13 | 5 |
| $C_3H_8$ | — | 4 | 1 | 8 |
| $C_3H_6$ | — | 3 | — | 1 |
| $i-C_4H_{10}$ | — | 12 | — | 13 |
| $n-C_4H_{10}$ | — | 2 | — | 2 |
| $i-C_5H_{12}$ | — | 16 | — | 15 |
| $n-C_5H_{12}$ | — | 7 | — | 1 |
| $i-C_6H_{14}$ | — | 20 | — | 13 |
| $n-C_6H_{14}$ | — | 1 | — | — |
| $C_6+$ | — | 8 | 1 | 17 |
| DME | — | 5 | — | 2 |

TABLE 6

| Example No. | 46 | 47 | 48 | 49 | 50 | 51 | 52 |
|---|---|---|---|---|---|---|---|
| Catalyst from Example No. | 16 | 16 | 17 | 17 | 18 | 12 | 12 |
| Temperature (°C.) | 399 | 399 | 405 | 405 | 393 | 399 | 399 |
| Pressure (atm.) | 34 | 34 | 34 | 34 | 34 | 34 | 34 |
| Gas feed rate (cc./hr./gm) | 1500 | 1600 | 1000 | 1050 | 1400 | 1000 | 1400 |
| Liquid feed rate (cc./hr./gm.) | — | 1.0 | — | 1.0 | — | — | 1.0 |
| Product Composition (Wt. %) | | | | | | | |
| $CH_4$ | 54 | 8 | 75 | 16 | 57 | 60 | 48 |
| $C_2H_6$—$C_2H_4$ | 4 | 3 | 19 | 10 | 4 | 7 | 4 |
| $C_3H_8$ | 6 | 4 | 4 | 7 | 4 | 19 | 22 |
| $C_3H_6$ | 2 | 2 | — | 5 | — | — | — |
| $i-C_4H_{10}$ | 12 | 25 | 1 | 7 | 4 | 2 | 2 |
| $n-C_4H_{10}$ | 2 | 3 | — | 3 | 2 | 3 | 5 |

TABLE 6-continued

| Example No. | 46 | 47 | 48 | 49 | 50 | 51 | 52 |
|---|---|---|---|---|---|---|---|
| i-$C_5H_{12}$ | 7 | 13 | 1 | 6 | 3 | 2 | 2 |
| n-$C_5H_{12}$ | — | — | — | 1 | 2 | — | — |
| i-$C_6H_{14}$ | 5 | 8 | — | 4 | 2 | 1 | 2 |
| n-$C_6H_{14}$ | — | 1 | — | — | — | — | — |
| $C_6+$ | 8 | 22 | 0 | 12 | 22 | 6 | 15 |
| DME | — | 10 | — | 29 | — | — | — |

TABLE 7

| Example No. | 53 | 54 | 55 | 56 | 57 | 58 |
|---|---|---|---|---|---|---|
| Catalyst from Example No. | 16 | 16 | 16 | 20 | 4 | 4 |
| Temperature (°C.) | 399 | 399 | 399 | 399 | 399 | 399 |
| Pressure (atm.) | 34 | 34 | 34 | 34 | 34 | 34 |
| Gas feed rate (cc./hr./gm.) | 1600 | 1050 | 800 | 1050 | 1000 | 1000 |
| Methanol feed rate (cc./hr./gm.) | 2.0 | — | 1.0 | — | — | 1.0 |
| Propylene feed rate (cc./hr./gm.) | — | 1.0 | 1.0 | 1.0 | 1.0 | 1.0 |
| Product Composition (Wt. %) | | | | | | |
| $CH_4$ | 4 | 1 | 3 | 1 | 1 | 2 |
| $C_3H_8$ | 5 | 50 | 15 | 30 | 20 | 8 |
| i-$C_4H_{10}$ | 30 | 12 | 25 | 13 | 21 | 7 |
| i-$C_5H_{12}$ | 17 | 9 | 17 | 14 | 11 | 4 |
| i-$C_6H_{14}$ | 11 | 12 | 9 | 27 | 19 | 8 |
| $C_6+$ | 20 | 10 | 17 | 13 | 19 | 61 |

TABLE 8

| Example No. | 59 | 60 | 61 | 62 | 63 |
|---|---|---|---|---|---|
| Day No. | 2 | 7 | 12 | 16 | 17 |
| Catalyst from Example No. | 8 | 8 | 8 | 8 | 8 |
| Temperature (°C.) | 385 | 402 | 414 | 414 | 416 |
| Pressure (atm.) | 34 | 34 | 34 | 34 | 34 |
| Gas feed rate (cc./hr./gm.) | 2750 | 2750 | 1300 | 1500 | 1000 |
| Liquid feed rate (cc./hr./gm.) | 1 | 1 | 1 | 1 | 1 |
| Product Composition (Wt. %) | | | | | |
| $CH_4$ | 7 | 4 | 6 | 12 | 15 |
| $C_2H_6$—$C_3H_8$ | 11 | 10 | 14 | 16 | 4 |
| i-$C_4H_{10}$ | 39 | 29 | 21 | 17 | 1 |
| i-$C_4H_{10}$ | 4 | 2 | 2 | 2 | — |
| i-$C_5H_{12}$ | 15 | 15 | 14 | 12 | 1 |
| n-$C_5H_{12}$ | — | — | — | — | — |
| $C_5+$ | 13 | 23 | 23 | 22 | 4 |
| DME | 8 | 14 | 16 | 14 | 71 |

Examples 23, 24, 26, 28, 33, 35, 36, 38, 42, 44, 46, 48, 50 and 51 involve the reaction between carbon monoxide and hydrogen. The results of these examples illustrate both a high selectivity for the production of branched hydrocarbons in this reaction relative to the production of unbranched hydrocarbons having the same number of carbon atoms, and the production of $C_5+$ and $C_6+$, which are primarily mixtures of branched hydrocarbons containing at least 6 carbon atoms and at least 7 carbon atoms, respectively. Comparison of the results for Exampls 23 and 24 illustrates that, when the catalyst is free of a thorium component, increases in the reaction pressure and in the space velocity of the total gaseous feed to the reactor result in decreases in the yield of methane and in increases in the yields of $C_5+$ and $C_6+$ and in the degree of conversion of carbon monoxide. By contrast, comparison of the results of Examples 35 and 36 indicates that, when the catalyst additionally contains a thorium component, an increase in the reaction pressure causes an increase in the yield of methane and a decrease in the yield of $C_6+$ material.

Examples 25, 27, 29–32, 34, 37, 39–41, 43, 45, 47, 49, 52–58 and 59–63 involve reactions between hydrogen and at least one of an alcohol containing from 1 to 6 carbon atoms and an olefin containing from 2 to 6 carbon atoms. Comparison of the results of Examples 25, 34, 39, 43, 45, 47, 49 and 52 with the results of Examples 24, 33, 38, 42, 44, 46, 48 and 51, respectively, illustrates that relatively smaller amounts of methane and relatively greater amounts of $C_6+$ are produced in the reaction between hydrogen and the alcohol and/or olefin than in the reaction between hydrogen and carbon monoxide. Furthermore, comparison of the results of Examples 27 and 37 with the results of Examples 25 and 34, respectively, illustrates that the relative yields of methane are further reduced and the relative yields of branched hydrocarbons are further increased as a result of the presence of a thorium component in the catalyst.

Comparison of the results of Examples 29–32, Examples 34 and 37, and Examples 39–40 illustrates that increases in the reaction pressure, or temperature, result in increases in the relative yield of methane and in decreases in the relative yields of branched hydrocarbons. Comparison of the results of Examples 53–58 indicate that the use of a feed containing both methanol and propylene, rather than a feed containing only propylene, results in less formation of propane from propylene and in enhanced yields of $C_6+$. Furthermore, when the catalyst employed was a composite of a cadmium-exchanged zeolite Y and alumina, the yield of branched hydrocarbons was increased when the feed comprised both methanol and propylene rather than propylene alone. In addition, the $C_6+$ fraction was substantially free of aromatics when the feed comprised only methanol or only propylene. However, when the feed comprised both methanol and propylene, the $C_6+$ fraction contained substantial amounts of aromatic materials, indicating synergism.

Examples 59–63 illustrate that catalytic activity in this reaction is maintained over a test period of 16 days, with the reaction temperature being increased 29° C. over that time span to partially offset decreases in catalytic activity. Catalytic activity decreases substantially at the seventeenth day. By contrast, a catalyst otherwise the same except not containing a cadmium component deactivates to an excessive degree in only 5 hours under substantially the same conditions.

From the above description, it is apparent that the objects of the present invention have been achieved. While only certain have been set forth, alternative embodiments and various modifications will be apparent from the above description to those skilled in the art. These and other alternatives are considered equivalents and within the spirit and scope of the present invention.

Having described the invention, what is claimed is:

1. A method for producing branched aliphatic hydrocarbons by reacting hydrogen with at least one of an alcohol containing from 1 to 6 carbons atoms and an olefin containing from 2 to 6 carbon atoms, at a temperature in the range of from about 300° C. to about 480° C., at a pressure in the range of from about 5 to about 150 kilograms per square centimeter, and in the presence of a catalyst composition comprising a cadmium component and a support material having acidic properties, wherein the cadmium component is in the form of the elemental metal, its oxide or salt or a combination thereof, wherein the cadmium component is present at a concentration level in the range of from about 0.1 to about 20 weight percent, calculated as cadmium oxide and based on the weight of the catalyst, and wherein the support comprises an amorphous refractory inorganic oxide, a pillared smectite or vermiculite clay, a molecular sieve consisting essentially of unexchanged or cation-exchanged chabazite, clinoptilolite, zeolite A, zeolite L, zeolite X, zeolite Y, ultrastable zeolite Y, or crystalline borosilicate molecular sieve, or a combination thereof.

2. The method of claim 1 wherein, if the alcohol is present, the mole ratio of alcohol-to-hydrogen is in the range of from about 10:1 to about 1:10, if the olefin is present, the mole ratio of olefin-to-hydrogen is in the range of from about 10:1 to about 1:10, and if both the alcohol and olefin are present, the mole ratio of alcohol-to-olefin is in the range of from about 10:1 to about 1:10.

3. The method of claim 1 wherein the alcohol comprises methanol, ethanol, propanol or a combination thereof.

4. The method of claim 1 wherein, where no alcohol is present, the olefin comprises propylene, butylene, amylene or a combination thereof.

5. The method of claim 1 wherein, when an alcohol is present, the olefin comprises ethylene, propylene, butylene or a combination thereof.

6. The method of claim 1 wherein the reaction is performed at a temperature in the range of from about 315° C. to about 425° C. a pressure of at least 10 kilograms per square centimeter and, if the alcohol is present, the mole ratio of the alcohol-to-hydrogen is in the range of from about 4:1 to about 1:4, if the olefin is present, the mole ratio of the olefin-to-hydrogen is in the range of from about 4:1 to about 1:1, and if both the alcohol and the olefin are present, the mole ratio of the alcohol-to-olefin is in the range of from about 3:1 to about 1:3.

7. The method of claim 1 wherein the space velocity of each of the alcohol and olefin that is present is in the range of from about 0.01 to about 0.1 moles per gram of catalyst per hour.

8. The method of claim 1 wherein the cadmium component is in the form of cadmium oxide.

9. The method of claim 1 wherein the cadmium component is present at a concentration level in the range of from about 1 to about 10 weight percent, calculated as cadmium oxide and based on the weight of the catalyst.

10. The method of claim 1 wherein the refractory inorganic oxide comprises alumina, zirconia, titania, an oxide of the lanthanide series, an oxide of the actinide series, a combination thereof, or a combination thereof with silica or magnesia.

11. The method of claim 1 wherein the molecular sieve is in the hydrogen- or rare earth-exchanged form.

12. The method of claim 1 wherein the borosilicate comprises a molecular sieve material having the following composition in terms of mole ratios of oxides:

$$0.9 \pm 0.2 M_{2/n}O : B_2O_3 : ySiO_2 : zH_2O$$

wherein M is at least one cation having a valence of n, y is between 4 and about 600, and z is between 0 and about 160, and providing an X-ray diffraction pattern comprising the following X-ray diffraction lines and assigned strengths:

| /d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

13. The method of claim 1 wherein the pillared smectite or vermiculite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

14. The method of claim 1 wherein the support comprises from about 20 to about 95 weight percent of an aforesaid refractory inorganic oxide and from about 5 to 80 percent of an aforesaid molecular sieve or pillared smectite or vermiculite clay.

15. The method of claim 1 wherein, when the alcohol is present, the support comprises cadmium-exchanged zeolite Y, rare earth-exchanged zeolite Y, ultrastable zeolite Y, a pillared smectite or vermiculite clay, silica-alumina, or crystalline borosilicate molecular sieve.

16. The method of claim 1 wherein, when the alcohol is not present, the support comprises cadmium-exchanged zeolite Y, rare earth-exchanged zeolite Y, ultrastable zeolite Y, or crystalline borosilicate molecular sieve.

17. The method of claim 1 wherein the catalyst comprises additionally a thorium component on the support wherein the thorium component is in the form of elemental thorium, its oxide or salt or a combination thereof and is present at a concentration in the range of from about 1 to about 25 weight percent, calculated as thorium oxide and based on the weight of the catalyst.

18. The method of claim 17 wherein the thorium component is in the form of thorium oxide.

19. The method of claim 17 wherein at least one reactant is an alcohol and the catalyst support is silica-alumina.

* * * * *

UNITED STATES PATENT OFFICE
CERTIFICATE OF CORRECTION

Patent No. 4,496,785　　　　　　　　　　　Dated January 29, 1985

Inventor(s) JEFFREY T. MILLER - NEVITT, THOMAS D.

It is certified that error appears in the above-identified patent and that said Letters Patent are hereby corrected as shown below:

| Column | Line | | |
|---|---|---|---|
| 12 | 44 | "300" | should be -- 3000 -- |
| 19 | 25 | " t " | should be -- T -- |
| 21 | 43 | "i-$C_4H_{10}$" | should be -- n-$C_4H_{10}$ -- |
| 24 | 33 | After "80" | Add -- weight -- |

Signed and Sealed this

Sixth Day of August 1985

[SEAL]

Attest:

DONALD J. QUIGG

Attesting Officer　　　Acting Commissioner of Patents and Trademarks